US006273086B1

(12) United States Patent
Ohki et al.

(10) Patent No.: US 6,273,086 B1
(45) Date of Patent: Aug. 14, 2001

(54) INHALANT MEDICATOR

(75) Inventors: Hisatomo Ohki; Yoshiyuki Yazawa; Shigemi Nakamura; Kazunori Ishizeki, all of Gunma; Akira Yanagawa, Yokohama, all of (JP)

(73) Assignees: Unisia Jecs Corporation, Atsugi; Dott Limited Company, Yokohama, both of (JP)

( * ) Notice: Subject to any disclaimer, the term of this patent is extended or adjusted under 35 U.S.C. 154(b) by 0 days.

(21) Appl. No.: 09/355,759
(22) PCT Filed: Jan. 28, 1999
(86) PCT No.: PCT/JP99/00356

§ 371 Date: Aug. 4, 1999

§ 102(e) Date: Aug. 4, 1999

(87) PCT Pub. No.: WO99/39761

PCT Pub. Date: Aug. 12, 1999

(30) Foreign Application Priority Data

Feb. 6, 1998 (JP) .................................................. 10-41410

(51) Int. Cl.[7] ......................... A61M 15/00; A61M 16/00

(52) U.S. Cl. ............................... 128/203.21; 128/203.12; 128/203.15; 128/205.21; 128/203.19; 604/58

(58) Field of Search ......................... 128/203.12, 203.15, 128/200.14, 200.24, 203.21, 203.25, 203.23, 203.24, 205.21, 203.19; 604/58

(56) References Cited

U.S. PATENT DOCUMENTS 3,906,950 * 9/1975 Cocozza .............................. 128/266
5,476,093 12/1995 Lankinen ............................ 128/203

FOREIGN PATENT DOCUMENTS 19522416 1/1997 (DE) .
745 402 12/1996 (EP) .
2 218 905 9/1974 (FR) .
7313599 12/1995 (JP) .
93/18811 9/1993 (WO) .

* cited by examiner

*Primary Examiner*—John G. Weiss
*Assistant Examiner*—Mital Patel
(74) *Attorney, Agent, or Firm*—Foley & Lardner

(57) ABSTRACT

An inhalant medicator comprises a medicator body having a granular medicine accommodation chamber and an inhalant port, and air passageways disposed in the medicator body and communicating the inhalant port via the granular medicine accommodation chamber to the atmosphere for supplying granular medicines into the inhalant port. Also provided is a granular medicine diffusion means located downstream of the granular medicine accommodation chamber for efficiently diffusing the granular medicines. A cylindrical adapter 10 is detachably installed in the inhalant port 9. The granular medicine diffusion means comprises a granular medicine diffusion chamber 11 formed in the adapter, an adapter inlet passageway tangentially radially extending from the circumference of the diffusion chamber 11 for creating turbulent flow in the diffusion chamber, and an adapter outlet passageway intercommunicating the diffusion chamber and the inhalant port and having a diametrically-enlarged outlet passage portion, for good dispersion of the granulated medicines flowing out of the diffusion chamber into the inhalant port.

4 Claims, 3 Drawing Sheets

INHALANT MEDICATOR

TECHNICAL FIELD

The invention relates to an inhalant medicator suitable to prescribe granulated medicines toward within lungs of a patient by way of breathing action of the patient.

BACKGROUND ART

Generally, there are two typical medications of prescribing granulated medicines toward within lungs of an asthmatic patient, that is, one being a medication that the granulated medicines are inhaled by way of a liquid aerosol atomizer, and the other being an inhalation treatment that very fine granular medicines encapsulated in a granular-medicine accommodation chamber or a capsule, such as granules each having a particle diameter ranging from 5 μm to 10 μm, are inhaled by breaking through the granular-medicine accommodation chamber or the capsule. Of these medications for an asthmatic patient, an inhalant medicator, used for the latter inhalation treatment where encapsulated granulated medicines are inhaled, has been disclosed in Japanese Patent Provisional Publication No. 7-313599.

The conventional inhalant medicator disclosed in the Japanese Patent Provisional Publication No. 7-313599 is generally comprised of a medicator body equipped at one axial end with a capsule housing hole (a granular medicine accommodation chamber) and at the other axial end with an inhalant port used for inhalation of granular medicines, an inflow air passageway having an axial inflow passage extending in the axial direction of the medicator body and a pin insertion hole extending in a radial direction of the medicator body for communicating the capsule housing hole with the atmosphere, an outflow air passageway having an outflow passage extending in the axial direction of the medicator body and a pin insertion hole extending in the radial direction of the medicator body for communicating the capsule housing hole with the inhalant port, and a pricking tool having pins insertable toward the capsule through the respective pin insertion holes for breaking through the capsule accommodated in the capsule housing hole. The inflow and outflow air passageways are provided for supplying the granular medicines encapsulated in the capsule into the inhalant port, while dispersing the granular medicines in the capsule by air flow flowing through the interior of the capsule.

In conventional inhalant medicators, when prescribing granulated medicines into the lungs of a patient, a capsule filled with the granulated medicines is, first of all, installed in a capsule housing hole. Then, through holes are pricked in the capsule by means of a pricking tool, with the result that the inflow side of the medicator body is communicated through the through holes pricked in the capsule with the outflow side, that is, the outflow air passageway and the inhalant port. Under this condition, when the patient draws his or her breath while taking the inhalant port in his or her mouth, the granular medicines stored in the capsule housing hole can be discharged into the inhalant port by way of the air flow sucked in the atmosphere side and then flowing through the inflow air passageway. In this manner, the granular medicines, flowing out of the capsule, could be inhaled into the lungs of the patient.

As discussed above, in the conventional inhalant medicators, granular medicines, stored in a capsule housing hole, are diffused or agitated by way of fluid flow of air flowing via the inflow air passageway into the capsule housing hole. However, during medication with a granular medicine having a strong condensation property (bad dispersion), or a powdered medicine having a greatly increased tendency to be charged with static electricity, or a powdered medicine containing oil content, or the like, there is a problem of unstable dispersion of the granular or powdered medicine from being inhaled toward within the lungs of the patient stably and satisfactorily at all times where medications are repeatedly made with medicines of different physical properties. In case of the use of granular or powdered medicines having the physical properties set out above, there is a possibility that a lump of granular or powdered medicines tend to be dropped in the oral cavity or the mouth of the patient during the inhalation without sufficient dispersion, thus preventing medical prescription of a specified amount of granulated or powdered medicines into the patient' lungs. This lowers medical benefits of the granulated or powdered medicines.

It is, therefore, in view of the previously-described disadvantages of the prior art, an object of the present invention to provide an inhalant medicator which is capable of prescribing a specified amount of granular or powdered medicines stored in a capsule or a medicator body toward within lungs of a patient by widely dispersing and micronizing the granular or powdered medicines.

DISCLOSURE OF THE INVENTION

In order to accomplish the aforementioned and other objects, according to the invention as claimed in claim 1, an inhalant medicator comprises a medicator body formed at one axial end with a granular medicine accommodation chamber and at another axial end with an inhalant port for inhalation of granular medicines, air passageways disposed in the medicator body and intercommunicating an atmosphere side and the inhalant port via the granular medicine accommodation chamber for supplying the granular medicines stored in the granular medicine accommodation chamber of the medicator body into the inhalant port, and a granular medicine diffusion means disposed in the medicator body and located downstream of the granular medicine accommodation chamber for diffusing the granular medicines, flowing out of the granular medicine accommodation chamber through the air passageways into the inhalant port. In the inhalant medicator made according to the invention defined in claim 1, when a patient draws his or her breath via the inhalant port, the granular medicines, flowing out of the granular medicine accommodation chamber through the air passageways, can be efficiently diffused by the granular medicine diffusion means, and whereby more efficiently micronized granular medicines can be flowed out into the inhalant port, and thus a specified amount of granular medicines can be reliably prescribed into lungs of the patient. This enhances medical virtue or benefits of the granular or powdered medicines, thus enhancing the reliability of the inhalant medicator.

According to the invention as claimed in claim 2, the medicator body has an adapter which is detachably installed in the inhalant port. The granular medicine diffusion means comprises a granular medicine diffusion chamber formed in the adapter and extending in an axial direction of the adapter, an adapter inlet passageway fluidly disposed between the granular medicine diffusion chamber and the air passageways for creating turbulent flow in the granular medicine diffusion chamber, and an adapter outlet passageway intercommunicating the granular medicine diffusion chamber and the inhalant port. In the inhalant medicator made according to the invention defined in claim 2, when the granular medicines flow into the granular medicine diffusion chamber through the adapter inlet passage, the granular medicines can be efficiently diffused and micronized by means of the turbulent flow created by the adapter inlet passage, and whereby the micronized granular medicines flow into the inhalant port via the adapter outlet passage. Various sorts of adapters having granular medicine diffusion chambers different from each other in shape, adapter inlet passages different from each other in shape, and/or adapter outlet passages different from each other in shape can be prepared, and one of the different sorts of adapters can be selectively installed on the medicator body. Therefore, a more proper adapter is selectable from the different sorts of adapters, depending upon physical properties of granular medicines, a vital capacity of a patient, or a weak chest or a strong chest. This highly enhances an efficiency of inhalation of granular medicines.

According to the invention as claimed in claim 3, the adapter inlet passageway of the granular medicine diffusion means comprises an inlet passage offsetting with respect to a central axis of the granular medicine diffusion chamber and extending radially tangentially from the circumference of the granular medicine diffusion chamber, and opening to the granular medicine diffusion chamber at an innermost end of the inlet passage. In the inhalant medicator made according to the invention defined in claim 3, air, entering through the adapter inlet passageway into the granular medicine diffusion chamber together with the granular medicines, effectively create turbulent flow in the granular medicine diffusion chamber. The turbulent flow efficiently diffuse and micronize the granular medicines. The radially tangentially extending adapter inlet passage is very simple, and thus the total construction of the inhalant medicator as well as the granular medicine diffusion means can be simplified. This enables easy cleaning of the inhalant medicator after medication.

According to the invention as claimed in claim 4, the adapter outlet passageway of the granular medicine diffusion means comprises a diametrically-enlarged outlet passage portion diametrically enlarged from the granular medicine diffusion chamber toward the inhalant port to an extent substantially identical to a size of opening of the inhalant port. Therefore, the granular medicines, flowing from the granular medicine diffusion chamber toward the inhalant port, can be effectively widely dispersed by means of the diametrically-enlarged outlet passage portion, and the widely dispersed granular medicines can be discharged into the inhalant port, and whereby the granular medicines can be more efficiently inhaled into the lungs of the patient.

According to the invention as claimed in claim 5, the air passageways comprise an inflow air passageway having an inflow passage extending in an axial direction of the medicator body and a radial bore extending in a radial direction of the medicator body for communicating the granular medicine accommodation chamber with the atmosphere, and an outflow air passageway having an outflow passage extending in the axial direction of the medicator body and a second radial bore extending in the radial direction of the medicator body for communicating the granular medicine accommodation chamber with the adapter inlet passageway. The adapter inlet passageway is fluidly disposed between the granular medicine diffusion chamber and the outflow air passageway. With the arrangement as recited in claim 5, the adapter inlet passageway can produce the turbulent flow in the granular medicine diffusion chamber.

According to the invention as claimed in claim 6, the adapter inlet passageway comprises a plurality of circumferentially-equidistant spaced inlet passages offsetting with respect to a central axis of the granular medicine diffusion chamber and extending radially tangentially from the circumference of the granular medicine diffusion chamber, and opening to the granular medicine diffusion chamber at their innermost ends. In the inhalant medicator made according to claim 6, entering through the adapter inlet passageway into the granular medicine diffusion chamber together with the granular medicines, more effectively create turbulent air flow in the granular medicine diffusion chamber, thus ensuring sufficient micronization of the granular medicines during medication. The radially tangentially extending adapter inlet passages are very simple in construction, thus enabling easy washing of the inhalant medicator after the medication.

DESCRIPTION OF THE PREFERRED EMBODIMENTS

The present invention will be hereinbelow described in detail in reference to the drawings (FIGS. 1 through 3) attached hereto.

Figure 1:
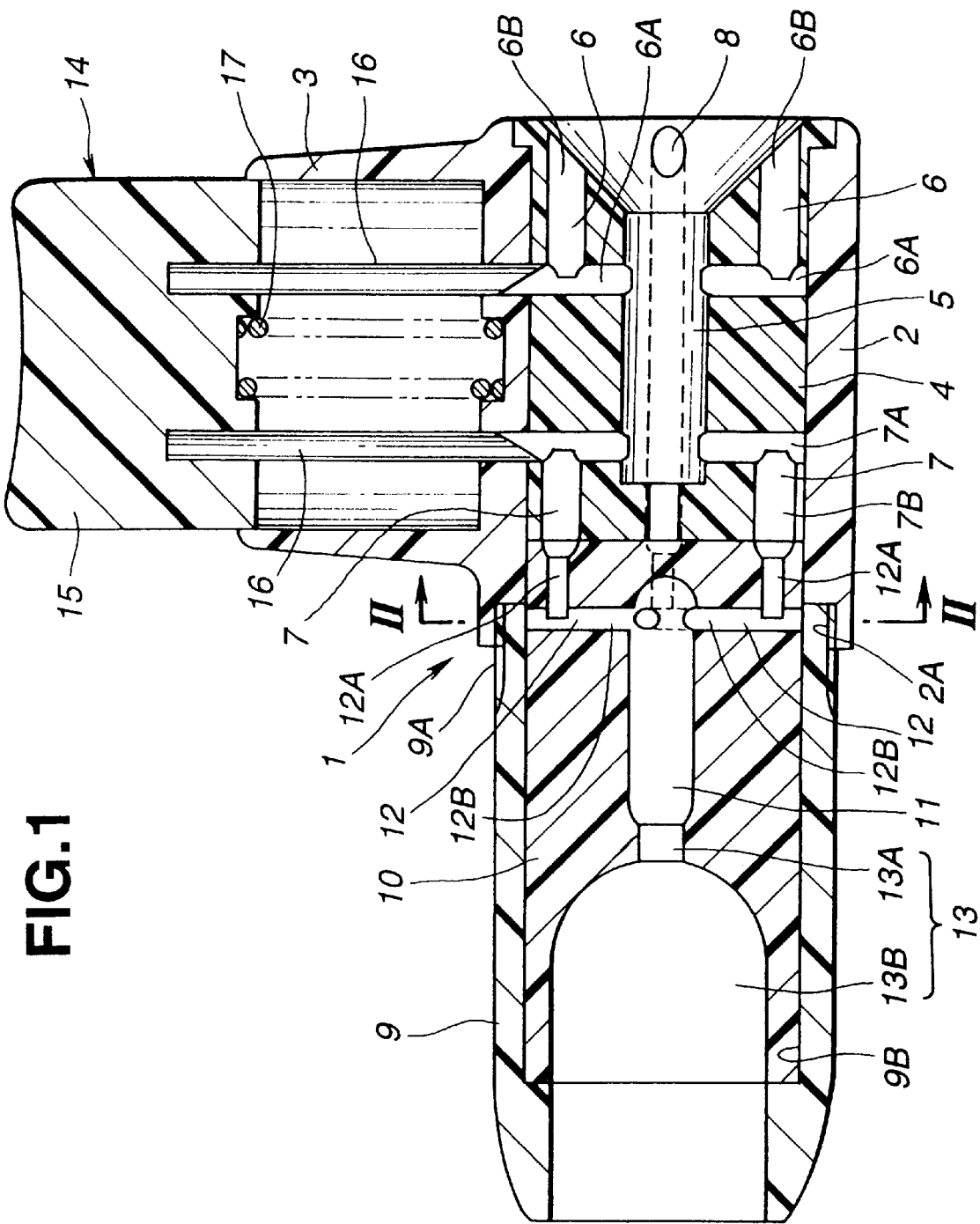
FIG. 1 is a cross-sectional view illustrating an embodiment of an inhalant medicator.
Figure 2:
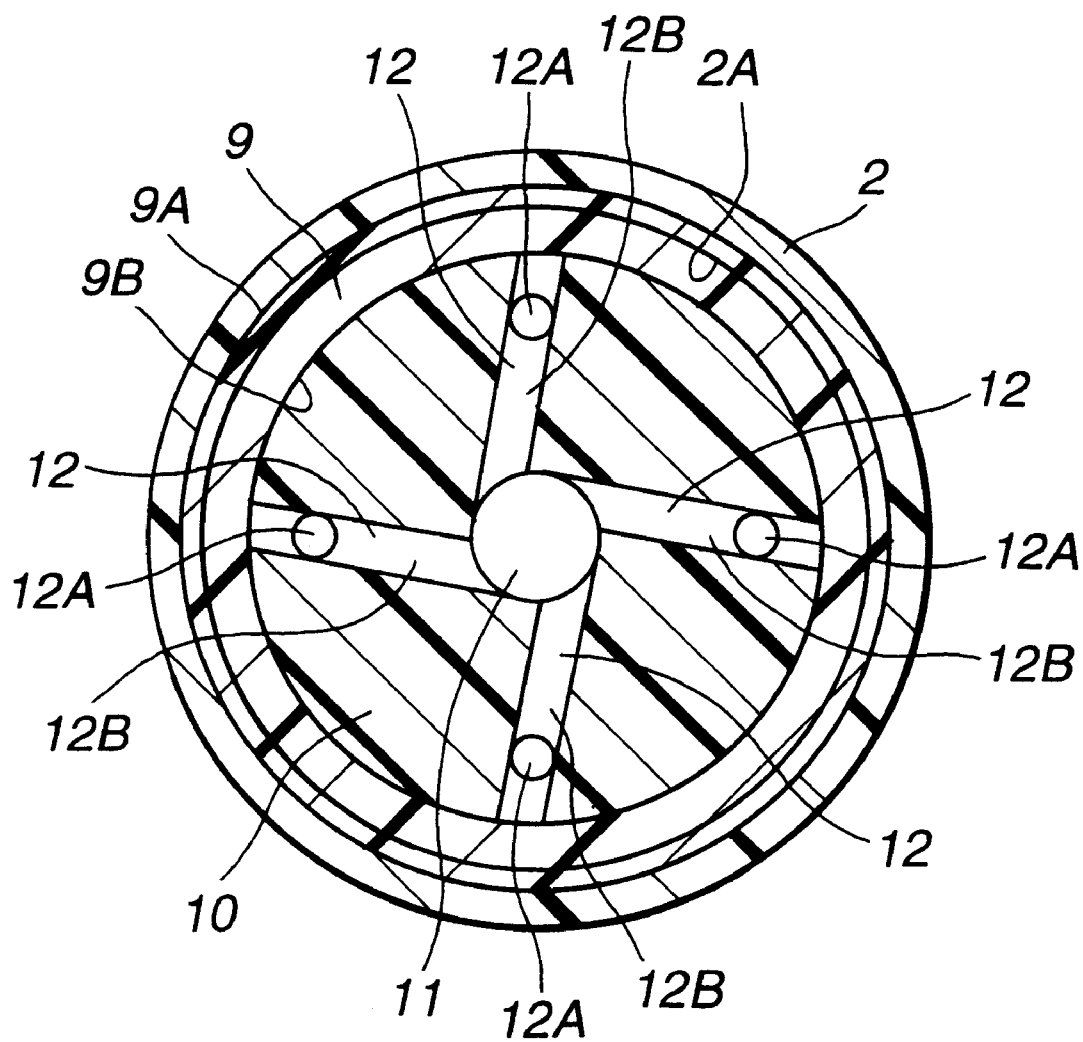
FIG. 2 is an enlarged lateral cross section of a medicator body, taken along the line II—II of FIG. 1, and enlarging a section of an adapter inlet passageway.
Figure 3:
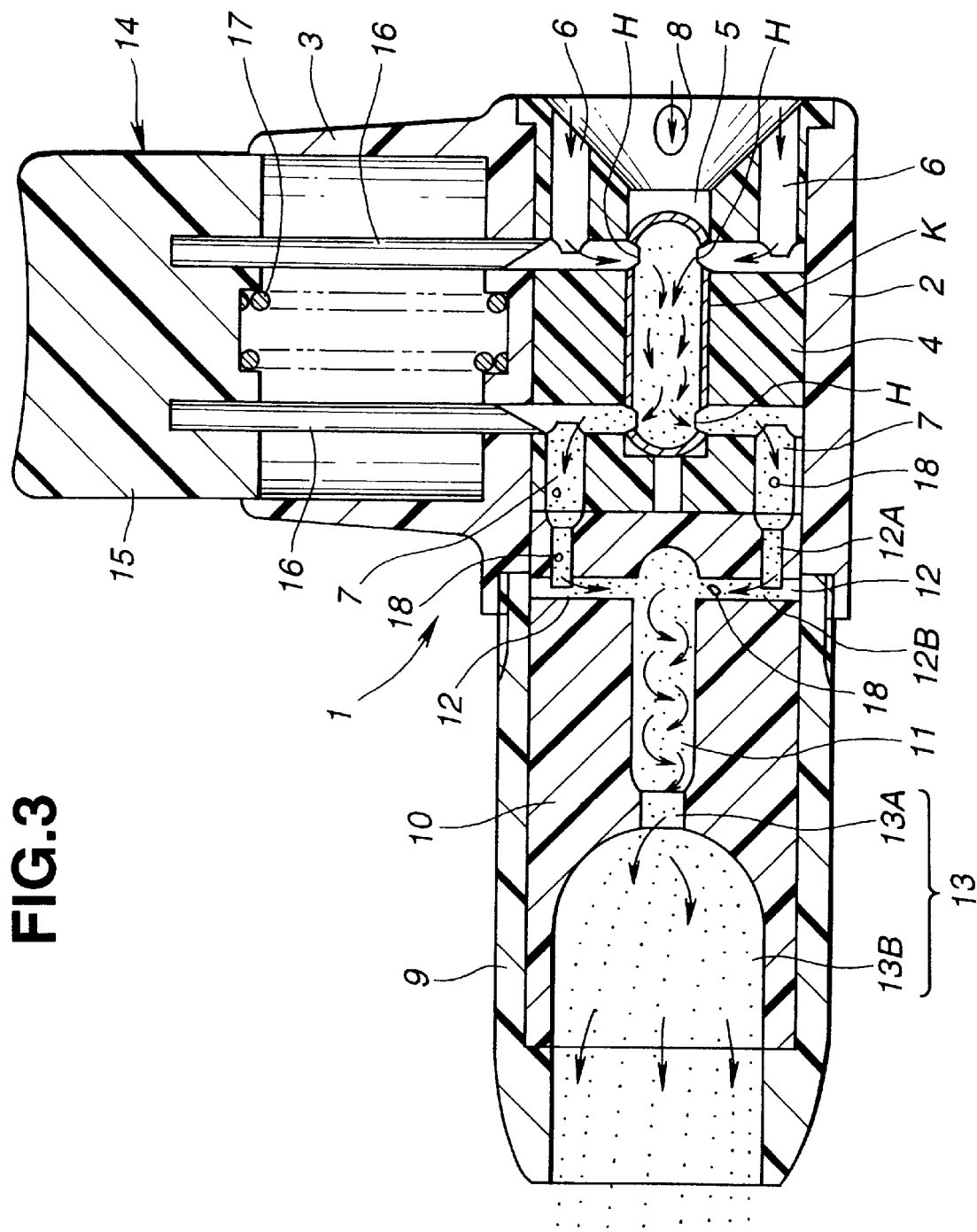
FIG. 3 is a cross section of the inhalant medicator of the embodiment in a particular state where the granular or powdered medicines enclosed in the capsule are inhaled by the patient.

Referring now to FIGS. 1 through 3, reference sign 1 denotes a medicator body constructing an essential part of the inhalant medicator. The medicator body 1 is comprised of a capsule holder accommodating portion 2, a capsule holder 4, a capsule housing chamber 5, an inhalant port 9, and an adapter 10. The capsule holder accommodating portion 2 is substantially cylindrical in shape. The holder accommodating portion 2 located in one half (the right-hand half) of the medicator body 1. The holder accommodating portion 2 is integrally formed with a cylindrical guide portion 3 on its outer periphery, such that the cylindrical guide portion 3 is projected radially outwardly from the outer periphery of the holder accommodating portion 2. As fully described later, the cylindrical guide portion 3 is provided to movably guide and support a pin support portion 15 of a pricking tool 14. As seen in FIG. 1, the holder accommodating portion 2 is also formed at another axial end with a female screw-threaded portion 2A with which a male screw-threaded portion of the inhalant port 9 is detachably threadably engaged. The capsule holder 4, installed in the holder accommodating portion 2, is cylindrical in shape. The capsule holder 4 is formed at its axial portion with the capsule housing chamber or hole 5, serving as a granular medicine accommodation chamber. A capsule K, which will be described later, is stored or accommodated in the capsule housing chamber 5. Reference signs 6, 6 denote two inflow air passageways formed in one axial end of the capsule holder 4. Each of the inflow air passageways 6, 6 are arranged around the capsule housing chamber 5. Each of the inflow air passageways 6, 6 comprises an axial inflow passage 6B arranged around the capsule housing chamber 5 and opening to the atmosphere through the opening end of the capsule holder 4, and a first radial pin insertion hole 6A communicating with the associated axial inflow passage 6B and extending radially in a manner so as to open to the capsule housing chamber 5. The first pin insertion hole 6A radially penetrates the capsule holder 4. The pin 16 of the pricking tool 14 is inserted into the capsule holder through the first pin insertion hole 6A, for pricking holes in the capsule K installed in the capsule housing chamber. The inflow passage 6B is formed in the capsule holder in such a manner as to open to the atmosphere, extending from the middle of the pin insertion hole 6A in one axial direction of the capsule holder. Reference signs 7, 7 denote two outflow air passageways formed in the other axial end of the capsule holder 4. Each of the outflow air passageways 7, 7 are arranged around the capsule housing chamber 5 to communicate with an adapter inlet passageway 12, which will be fully described later. Each of the outflow air passageways 7, 7 comprises an outflow passage 7B extending in the axial direction of the capsule holder, and a second radial pin insertion hole 7A communicating with the associated outflow passage 7B and extending radially in a manner so as to open to the capsule housing chamber 5. The second pin insertion hole 7A radially penetrates the capsule holder 4. The pin 16 of the pricking tool 14 is inserted into the capsule holder through the second pin insertion hole 7A, for pricking holes in the capsule K installed in the capsule housing chamber. The outflow passage 7B is formed in the capsule holder in such a manner as to open to an axial passage 12A of the adapter 10, extending from the middle of the pin insertion hole 7A in the other axial direction of the capsule holder. Reference signs 8, 8 denote two auxiliary air passages (in FIG. 1, only one auxiliary air passage is illustrated) arranged around the capsule housing chamber 5 and axially bored in the capsule holder 4 in a manner as to axially penetrate the capsule holder. As best seen in FIG. 1, each of the auxiliary air passages 8, 8 is formed in such a manner as to extend in the axial direction of the capsule holder at an angular position rotated by 90 degrees with respect to the respective inflow passage or to the respective outflow passage. The downstream ends of the auxiliary air passages 8 and 8 communicate the adapter inlet passageway 12 of the adapter 10. Reference sign 9 denotes the inhalant port located at and fitted to the left-hand end of the holder accommodating portion 2. The inhalant port 9 is substantially cylindrical in shape. The inhalant port 9 is formed at its joint end with a male screw-threaded portion 9A onto which a female screw-threaded portion 2A of the holder accommodating portion 2 is threadably received. The free end (the left-hand end) of the inhalant port 9 is gradually diametrically diminished for the purpose of easily holding the inhalant port in his or her mouth. The inhalant port 9 is formed with a substantially cylindrical two-stepped internal space. As seen in FIG. 1, the adapter 10 is installed in the substantially cylindrical two-stepped internal space of the inhalant port 9 so that the left-hand end of the adapter is fitted to the stepped portion 9B of the two-stepped internal space of the inhalant port 9. The adapter 10 is substantially cylindrical in shape. Almost all of the adapter 10 is accommodated in the cylindrical two-stepped internal space of the inhalant port 9, whereas part of the right-hand end of the adapter 10 is located in the holder accommodating portion 2 such that the right-hand end of the adapter 10 abuts the capsule holder 4. Reference sign 11 denotes the granular medicine diffusion chamber formed along the central axis of the adapter 10. The granular medicine diffusion chamber 11 is formed as an axially-extending cylindrical space, for the purpose of creating whirling flow or vortex flow in the granular medicine diffusion chamber 11 by means of air flow flowing through each of adapter inlet passageways 12 into the granular medicine diffusion chamber 11. In the shown embodiment, four adapter inlet passageways 12, 12, 12, 12 are formed in the right-hand end of the adapter 10. As appreciated from the cross section shown in FIG. 2, the four adapter inlet passageways 12, 12, 12, 12 are comprised of four axial passages 12A, 12A, 12A, 12A which are circumferentially 90°-spaced each other and axially bored in the right-hand end of the adapter and coaxially located with respect to the axis of the adapter 10, and four radial passages 12B, 12B, 12B, 12B which are radially bored in the right-hand end of the adapter and offsetting with respect to the central axis of the granular medicine diffusion chamber, and extend radially tangentially from the circumference of the granular medicine diffusion chamber, and open to or communicate with the granular medicine diffusion chamber at their innermost end and communicate with the respective axial passages 12A, 12A, 12A, 12A. In more detail, the central axial line of one of the radial passages 12B, 12B, 12B, 12B is slightly inclined from a line radially drawn through the axis of the granular medicine diffusion chamber 11 and passing through the center of the outermost end of the one radial passage 12B, in such a manner as to extend tangentially from the circumference of the granular medicine diffusion chamber 11 and opens to the granular medicine diffusion chamber 11 at the innermost end thereof. Of these axial passages 12A, 12A, 12A, 12A, a first diametrically-opposing pair of axial passages (corresponding to upper and lower axial passages 12B and 12B in FIGS. 1 and 2), point-symmetrical with respect to the axis of the adapter 10, are axially bored in the adapter in a manner so as to communicate with the respective axial outflow passages 7B and 7B of the outflow air passageways 7 and 7. On the other hand, a second diametrically-opposing pair of axial passages (corresponding to left and right axial passages 12B and 12B in FIG. 2), point-symmetrical with respect to the axis of the adapter 10, are axially bored in the adapter in a manner so as to communicate with the respective axially-extending auxiliary air passageways 8 and 8. As best seen in FIG. 3, when the air flow entering into the axial passages 12A, are introduced through the radial passages 12B into the granular medicine diffusion chamber 11 owing to the breathing action of the patient during medication, the respective adapter inlet passageways 12 create whirling air flow (turbulent flow) within the granular medicine diffusion chamber 11, and thereby efficiently diffuse the granular medicines supplied into the inhalant port by virtue of the air flow. Reference sign 13 denotes an axially-extending adapter outlet passageway formed at the downstream end (the left-hand end) of the adapter 10. The adapter outlet passageway 13 comprises an axially-extending small-diameter outlet passage (simply a small-diameter passage) 13A communicating with the downstream end of the granular medicine diffusion chamber 11 having an inside diameter less than an inside diameter of the granular cylindrical medicine diffusion chamber 11, and an axially-extending diametrically-enlarged passage (simply a diametrically-enlarged passage) 13B diametrically enlarged and bored in the left-hand end of the adapter 10 from the small-diameter passage 13A toward the opening end of the inhalant port 9. As seen in FIG. 1, the diametrically-enlarged passage 13B is rapidly diametrically enlarged and formed in the left-hand end of the adapter 10, so that the inside diameter of the diametrically-enlarged passage 13B is rapidly increased in the direction of the opening end of the inhalant port 9 up to approximately the same inside diameter as the opening end of the inhalant port 9. Thus, the rapidly, diametrically-enlarged passage 13B serves to widely efficiently disperse the granular medicines flowing out of the granular medicine diffusion chamber 11 into the inhalant port 9. As discussed above, a granular medicine diffusion means is constructed by the granular medicine diffusion chamber, each of the adapter inlet passageways 12, and the adapter outlet passageway 13. With the previously-described arrangement, when the air flow incoming through the outflow air passageways 7 and 7, and the auxiliary air passageways 8 and 8, flows via the adapter inlet passageways 12, 12, 12, 12 into the granular medicine diffusion chamber 11, the granular medicine diffusion means acts to create whirling flow or turbulent flow within the granular medicine diffusion chamber 11 owing to slight inclination of each of the radial passages 12B, 12B, 12B, 12B, and whereby the granular medicines supplied through the adapter inlet passageways 12 communicating the outflow air passageways 7 and 7 can be more efficiently diffused and micronized. Furthermore, when the micronized granular medicines flow through the small-diameter passage 13A and the diametrically-enlarged passage 13B included in the adapter outlet passageway 13 toward the opening end of the inhalant port 9, the micronized granular medicines can be more efficiently widely dispersed by way of the small-diameter passage 13A plus the diametrically-enlarged passage 13B. Thus, the granular medicines can be carried toward the opening end of the inhalant port 9 in a state of the granular medicines widely dispersed. In FIGS. 1 and 3, reference sign 14 denotes a pricking tool used for pricking holes (through openings) H in the capsule K accommodated in the capsule housing chamber 5. The pricking tool 14 comprises a pin support portion 15 movably supported within the cylindrical guide portion 3, two pins 16 and 16 fixedly connected at their bottom ends to the pin support portion 15 and located or fitted at their tips into the respective pin insertion holes 6A and 7A formed in the capsule holder 5, and a return spring 17 operably disposed between the pin support portion 15 and the holder accommodating portion 2. The return spring 17 permanently biases the pin support portion 15 in a direction that the pins 16 and 16 move apart from the capsule K, in order to return the pins to their initial positions after pricking the holes H in the capsule K. In order to make four through holes (or four through openings) H in the capsule K, the pin support portion 15 of the pricking tool 14 is first pushed into the cylindrical guide portion 3 against the bias of the return spring 17, and thus the tips of the pins 16 and 16 are inserted into the respective pin insertion holes 6A and 7A and thus penetrate the capsule K accommodated in the capsule housing chamber 5. In this manner the four through holes H can be formed in the capsule K by way of one push of the pin support portion 15. Thereafter, upon removal of the pushing force applied to the pin support portion 15 and the pins 16 and 16 are returned to their initial positions by way of the bias of the spring 17.

Hereinbelow described in detail the preparatory operation of the inhalant medication through which the patient inhales the granular medicines, and the flow of air and granular medicines during inhalation.

As regards the preparatory operation of the inhalant medication, first of all, a capsule K is inserted into and accommodated in the capsule housing chamber 5 from the opening end of the capsule holder 4. With the capsule K enclosed in the capsule housing chamber 5, when the pin support portion 15 of the pricking tool 14 is pushed into the cylindrical guide portion 3 along the inner peripheral wall of the guide portion 3, the pins 16, 16 are radially inwardly inserted along the respective pin insertion holes 6A and 7A, thus pricking four through holes H in the capsule K with the pins 16, 16. After the formation of the four through holes H in the capsule K, the pin support portion 15 and the pins 16, 16 can be returned to their initial positions by means of the return spring 17.

Hereunder discussed by reference to FIG. 3 is the detailed flow of air and granular medicines carried through the internal space or the internal flow passages of the inhalant medicator when the patient inhales the granular medicines. The patient draws his or her breath while taking the tapered end (the left-hand side opening end) of the inhalant port 9, and whereby the air flows from the inflow air passageways 6, 6 (including the axial inflow passages 6B, 6B and the first radial pin insertion holes 6A, 6A) through the right-hand side through holes H, H into the capsule K, thus diffusing granular medicines in the capsule K. The air containing the granular medicines flows out of the capsule K via the left-hand side through holes H and H into the outflow air passageways 7 and 7 (including the second radial pin insertion holes 7A, 7A and the axial outflow passages 7B, 7B). At this time, several insufficiently-diffused massive granular medicines 18, 18, . . . , 18 are often contained in the granular medicines flowing out of the capsule K into the outflow air passageway 7 and 7. Thereafter, the air flow containing the granular medicines, flowing into the outflow air passageways 7 and 7, enters via the axial passages 12A of the adapter inlet passageways 12 and the radial passages 12B into the granular medicine diffusion chamber 11. As previously described, when the air containing the granular medicines passes through the granular medicine diffusion chamber 11, the massive granular medicines 18 contained in the air flow can be further diffused and micronized owing to whirling flow (turbulent flow) created by the radial passages 12B. Additionally, a more strong whirling air flow can be created within the granular medicine diffusion chamber 11 by virtue of auxiliary air flow drawn into the granular medicine diffusion chamber 11 through the auxiliary air passageways 8 and 8 formed in the capsule holder 4 and via the associated adapter inlet passageways 12 and 12. Then, the granular medicines, diffused and micronized within the granular medicine diffusion chamber 11, flow out into the diametrically-enlarged passage 13B through the small-diameter passage 13A. As a result, the micronized granular medicines can be efficiently and widely dispersed by means of the diametrically-enlarged passage 13B combined with the small-diameter passage 13A. Thus, the granular medicines are carried into the inhalant port 9 in a state of the granular medicines widely satisfactorily dispersed, and then the sufficiently dispersed granular medicines are efficiently inhaled from the inhalant port 9 via the oral cavity of the patient into the lungs.

As set out above, in the inhalant medicator of the embodiment, the granular medicine diffusion chamber 11 is disposed and located downstream of the capsule housing chamber 5, and also whirling flow or turbulent flow can be created within the granular medicine diffusion chamber 11 by way of air flow flowing out of the adapter inlet passageways 12. Thus, the granular medicines flowing out of the capsule K together with the air flow passing through the interior of the capsule K can be further diffused by way of the whirling flow occurring in the granular medicine diffusion chamber 11, thereby more effectively micronizing massive granular medicines 18, and thus ensuring and facilitating medical prescription of a specified amount of granular medicines into the lungs of the patient. Additionally, the adapter 10 is detachably disposed in the cylindrical internal space of the inhalant port 9, and also the adapter 10 is formed with the granular medicine diffusion chamber 11, the adapter inlet passageways 12, and the adapter outlet passageway 13, constructing the granular medicine diffusion means. Various sorts of adapters having granular medicine diffusion chambers different from each other in shape, adapter inlet passages different from each other in shape, and/or adapter outlet passages different from each other in shape can be prepared, and one of the different sorts of adapters can be selectively installed on the medicator body, and therefore, a more proper adapter is selectable from the different sorts of adapters, depending upon physical properties of granular medicines used, a vital capacity of a patient (the subject of medication), or a weak chest or a strong chest. This highly enhances an efficiency of inhalation of granular medicines. Also, the radial passage 12B of the adapter inlet passageway 12 is slightly inclined in the tangential direction in order to create whirling flow or turbulent flow within the granular medicine diffusion chamber 11 during breathing action of the patient. Therefore, the granular medicine diffusion means is relatively simple in construction, thereby enabling easy cleaning of the medicator body of the inhalant medicator. Furthermore, in the shown embodiment, the adapter outlet passageway 13 comprises the diametrically-enlarged passage 13B, and the diametrically-enlarged passage 13B is rapidly enlarged in the direction of the opening end of the inhalant port 9. Thus, the granular medicines, flowing out of the granular medicine diffusion chamber 11 together with the air flow, can be widely dispersed in the inhalant port 9. This insures a more effective inhalation of granular medicines into the lungs of the patient.

In the inhalant medicator of the embodiment, a particular case where there is a one-to-one correspondence between the four adapter inlet passageways 12, 12, 12, 12 and the two outflow air passageways 7, 7 and the two auxiliary air passageways 8, 8 is exemplified. Alternatively, one of the two auxiliary air passageways 8 and 8 may be deleted to provide only one auxiliary air passageway 8, and additionally three adapter inlet passageways 12, 12, 12 may be formed in the adapter 10 in a manner so as to respectively communicate with the two outflow air passageways 7, 7 and the sole auxiliary air passageway 8. In case of a patient having a strong chest, the two auxiliary air passageways 8 and 8 may be all deleted, since there is no necessity of auxiliary air passages, and therefore only two adapter inlet passageways 12, 12 may be formed in the adapter 10 in a manner so as to respectively communicate with the two outflow air passageways 7, 7. In the embodiment, the granular medicine diffusion chamber 11 is formed in the adapter 10 at the confluent portion of the downstream ends of the radial passages 12B of the adapter inlet passageways 12. In lieu thereof, an intermediate portion of each of the outflow air passageways 7 and 7, or an intermediate portion of each of the adapter inlet passageways 12, 12, 12, and 12 may be formed as an enlarged volumetric-capacity chamber serving as a granular medicine diffusion chamber. Moreover, in the embodiment, the capsule holder 4 and the holder accommodating portion 2 are integrally connected and are detachable with each other. The capsule housing chamber 5 is defined capsule holder 4. A capsule K, filled with granular medicines, is accommodated in the capsule housing chamber 5. Alternatively, the capsule holder 4 may be deleted, and in lieu thereof a granular medicine accommodation chamber is formed directly in the medicator body. In this case, granular medicines can be charged directly into the granular medicine accommodation chamber and inhaled without any pricking work. This eliminates the necessity of the capsule K and the pricking tool 14.

While the foregoing is a description of the preferred embodiments carried out the invention, it will be understood that the invention is not limited to the particular embodiments shown and described herein, but that various changes and modifications may be made without departing from the scope or spirit of this invention as defined by the following claims.

INDUSTRIAL APPLICABILITY

As set forth above, an inhalant medicator made according to the invention is useful for the purpose of efficiently prescribing a specified amount of granular or powdered medicines toward within lungs of a patient, while widely dispersing and micronizing the granular or powdered medicines. Also, the inhalant medicator of the invention is useful for the purpose of efficiently prescribing granular or powdered medicines toward within lungs of a patient during medication, irrespective of physical properties of the granular medicines and/or the difference of vital capacity between an adult and a child (or weak or strong chests).

what is claimed is:

1. An inhalant medicator comprising:
   a medicator body formed at one axial end with a granular medicine accommodation chamber and at another axial end with an inhalant port for inhalation of powder and granular medicines;
   air passageways disposed in the medicator body and intercommunicating an atmosphere side and the inhalant port via the granular medicine accommodation chamber for supplying the powder and granular medicines stored in the granular medicine accommodation chamber of the medicator body into the inhalant port; and
   a granular medicine diffusion means disposed in the medicator body and located downstream of the granular medicine accommodation chamber for diffusing the powder and granular medicines, flowing out of the granular medicine accommodation chamber through the air passageways into the inhalant port;
   the medicator body having an adapter detachably installed in the inhalant port;
   the granular medicine diffusion means comprising a granular medicine diffusion chamber formed in the adapter and extending in an axial direction of the adapter, an adapter inlet passageway fluidly disposed between the granular medicine diffusion chamber and the air passageways for creating turbulent flow in the granular medicine diffusion chamber and an adapter outlet passageway intercommunicating the granular medicine diffusion chamber and the inhalant port; and
   the adapter inlet passageway of the granular medicine diffusion means comprising an inlet passage offsetting with respect to a central axis of the granular medicine diffusion chamber and extending radially tangentially from a circumference of the granular medicine diffusion chamber, and opening to the granular medicine diffusion chamber at an innermost end of the inlet passage.

2. The inhalant medicator as claimed in claim 1, wherein the adapter outlet passageway of the granular medicine diffusion means comprises a diametrically-enlarged outlet passage portion diametrically enlarged from the granular medicine diffusion chamber toward the inhalant port to an extent substantially identical to a size of opening of the inhalant port.

3. An inhalant medicator comprising:
   a medicator body formed at one axial end with a granular medicine accommodation chamber and at another axial end with an inhalant port for inhalation of powder and granular medicines;

air passageways disposed in the medicator body and intercommunicating an atmosphere side and the inhalant port via the granular medicine accommodation chamber for supplying the powder and granular medicines stored in the granular medicine accommodation chamber of the medicator body into the inhalant port; and a granular medicine diffusion means disposed in the medicator body and located downstream of the granular medicine accommodation chamber for diffusing the powder and granular medicines, flowing out of the granular medicine accommodation chamber through the air passageways into the inhalant port;

the medicator body having an adapter detachably installed in the inhalant port;

the granular medicine diffusion means comprising a granular medicine diffusion chamber formed in the adapter and extending in an axial direction of the adapter, an adapter inlet passageway fluidly disposed between the granular medicine diffusion chamber and the air passageways for creating turbulent flow in the granular medicine diffusion chamber, and an adapter outlet passageway intercommunicating the granular medicine diffusion chamber and the inhalant port; and the air passageways comprising an inflow air passageway having an inflow passage extending in an axial direction of the medicator body and a radial bore extending in a radial direction of the medicator body for communicating the granular medicine accommodation chamber with the atmosphere, and an outflow air passageway having an outflow passage extending in the axial direction of the medicator body and a second radial bore extending in the radial direction of the medicator body for communicating the granular medicine accommodation chamber with the adapter inlet passageway.

4. An inhalant medicator comprising:

a medicator body formed at one axial end with a granular medicine accommodation chamber and at another axial end with an inhalant port for inhalation of powder and granular medicines;

air passageways disposed in the medicator body and intercommunicating an atmosphere side and the inhalant port via the granular medicine accommodation chamber for supplying the powder and granular medicines stored in the granular medicine accommodation chamber of the medicator body into the inhalant port; and a granular medicine diffusion means disposed in the medicator body and located downstream of the granular medicine accommodation chamber for diffusing the powder and granular medicines, flowing out of the granular medicine accommodation chamber through the air passageways into the inhalant port;

the medicator body having an adapter detachably installed in the inhalant port;

the granular medicine diffusion means comprising a granular medicine diffusion chamber formed in the adapter and extending in an axial direction of the adapter, and adapter inlet passageway fluidly disposed between the granular medicine diffusion chamber and the air passageways for creating turbulent flow in the granular medicine diffusion chamber, and an adapter outlet passageway intercommunicating the granular medicine diffusion chamber and the inhalant port; and the adapter inlet passageway comprising a plurality of circumferentially-equidistant spaced inlet passages offsetting with respect to a central axis of the granular medicine diffusion chamber and extending radially tangentially from the circumference of the granular medicine diffusion chamber, and opening to the granular medicine diff-usion chamber at their innermost ends.

* * * * *